(12) United States Patent
Morita

(10) Patent No.: US 11,717,144 B2
(45) Date of Patent: Aug. 8, 2023

(54) ENDOSCOPE APPARATUS, OPERATING METHOD OF ENDOSCOPE APPARATUS, AND INFORMATION STORAGE MEDIUM

(71) Applicant: OLYMPUS CORPORATION, Tokyo (JP)

(72) Inventor: Yasunori Morita, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 494 days.

(21) Appl. No.: 17/093,770

(22) Filed: Nov. 10, 2020

(65) Prior Publication Data
US 2021/0052153 A1    Feb. 25, 2021

Related U.S. Application Data

(63) Continuation of application No. PCT/JP2018/021503, filed on Jun. 5, 2018.

(51) Int. Cl.
*A61B 1/06* (2006.01)
*A61B 1/04* (2006.01)
(Continued)

(52) U.S. Cl.
CPC ...... *A61B 1/0638* (2013.01); *A61B 1/000094* (2022.02); *A61B 1/042* (2013.01);
(Continued)

(58) Field of Classification Search
None
See application file for complete search history.

(56) References Cited

U.S. PATENT DOCUMENTS

2013/0293693 A1    11/2013  Igarashi et al.
2016/0089010 A1*   3/2016   Aoyama .............. A61B 1/0684
                                                         348/70
(Continued)

FOREIGN PATENT DOCUMENTS

JP    2001-170009 A    6/2001
JP    5362149 B1      12/2013
(Continued)

OTHER PUBLICATIONS

International Search Report dated Sep. 4, 2018 issued in PCT/JP2018/021503.

*Primary Examiner* — John P Leubecker
*Assistant Examiner* — Jae Woo
(74) *Attorney, Agent, or Firm* — Scully, Scott, Murphy & Presser, P.C.

(57) ABSTRACT

An endoscope apparatus includes an illumination device generating illumination light including a first light, a second light, and a third light, an imaging device capturing an image based on return light from biological tissue, and a processor configured to perform image processing based on first, second, and third images respectively corresponding to the first light, the second light, and the third light. The first light has a peak wavelength within a predetermined wavelength range including a wavelength achieving a largest value of a hemoglobin absorption coefficient. The second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value. The third light has a peak wavelength between the peak wavelengths of the first light and the second light.

12 Claims, 4 Drawing Sheets

(51) Int. Cl.
  *A61B 1/313* (2006.01)
  *A61B 5/1459* (2006.01)
  *A61B 1/00* (2006.01)
(52) U.S. Cl.
  CPC ............ *A61B 1/044* (2022.02); *A61B 1/3137* (2013.01); *A61B 5/1459* (2013.01)

(56) References Cited

U.S. PATENT DOCUMENTS

| | | | |
|---|---|---|---|
| 2017/0281140 A1* | 10/2017 | Arahira | A61B 1/3137 |
| 2018/0279853 A1* | 10/2018 | Daidoji | H04N 13/257 |
| 2018/0289246 A1* | 10/2018 | Tabata | A61B 1/044 |
| 2019/0005641 A1 | 1/2019 | Yamamoto | |
| 2019/0038111 A1 | 2/2019 | Endo | |
| 2019/0110672 A1* | 4/2019 | Onobori | A61B 1/0653 |
| 2019/0208986 A1 | 7/2019 | Saito | |
| 2019/0216305 A1* | 7/2019 | Fukuda | A61B 1/00 |
| 2019/0223703 A1* | 7/2019 | Fukuda | A61B 1/044 |
| 2019/0239736 A1 | 8/2019 | Aoyama | |
| 2021/0052153 A1* | 2/2021 | Morita | A61B 1/3137 |
| 2021/0145266 A1* | 5/2021 | On | G06T 7/174 |
| 2022/0192470 A1* | 6/2022 | Makino | A61B 1/044 |

FOREIGN PATENT DOCUMENTS

| | | |
|---|---|---|
| JP | 2016-067706 A | 5/2016 |
| JP | 2016-67775 A | 5/2016 |
| JP | 2017-158670 A | 9/2017 |
| JP | 2017-192565 A | 10/2017 |
| JP | 2018-38675 A | 3/2018 |
| JP | 2018-51065 A | 4/2018 |
| WO | 2018/079116 A1 | 5/2018 |

\* cited by examiner

ENDOSCOPE APPARATUS, OPERATING METHOD OF ENDOSCOPE APPARATUS, AND INFORMATION STORAGE MEDIUM

CROSS REFERENCE TO RELATED APPLICATION

This application is a continuation of International Patent Application No. PCT/JP2018/021503, having an international filing date of Jun. 5, 2018, which designated the United States, the entirety of which is incorporated herein by reference.

BACKGROUND

Inflammatory diseases of a stomach include various diseases such as gastritis or scirrhous stomach cancer. These diseases are diagnosed based on findings in image observation using an endoscope apparatus. For example, gastritis having atrophic mucosa is diagnosed by checking a blood vessel image in a white light image. Gastritis having thickening mucosa is diagnosed by confirming that folds of a stomach wall do not disappear when the stomach is expanded by supplied air. The scirrhous stomach cancer is diagnosed by checking a running shape and density of the folds of the stomach wall and confirming that a space between the folds is not widened when the stomach is expanded by supplied air.

Methods of diagnostic support by devising a wavelength of a light source or image processing in an endoscope apparatus are disclosed by Japanese Unexamined Patent Application Publication No. 2001-170009, Japanese Patent No. 5362149, and Japanese Unexamined Patent Application Publication No. 2016-67775, for example.

Japanese Unexamined Patent Application Publication No. 2001-170009 discloses a method called NBI (Narrow Band Imaging). In NBI, blue narrowband light and green narrowband light are used as illumination light to observe inflammation of mucosa or the like. Japanese Patent No. 5362149 and Japanese Unexamined Patent Application Publication No. 2016-67775 disclose methods for observing blood vessels in a layer deeper than mucosa by using illumination light having a center wavelength of around 600 nm.

SUMMARY

According to one aspect of the disclosure, there is provided an endoscope apparatus comprising:
an illumination device configured to generate illumination light including a first light, a second light, and a third light;
an imaging device configured to capture an image based on return light from biological tissue irradiated with the illumination light; and
a processor configured to perform image processing based on a first image, second image, and third image, respectively corresponding to the first light, second light, and third light, captured by the imaging device;
wherein the illumination device generates
the first light having a peak wavelength within a predetermined wavelength range including a wavelength achieving a largest value of a hemoglobin absorption coefficient,
the second light having a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and
the third light having a peak wavelength between the peak wavelength of the first light and the peak wavelength of the second light, and involving a larger scattering coefficient in the biological tissue than a scattering coefficient of the second light.

According to another aspect of the disclosure, there is provided an operating method of an endoscope apparatus, wherein
a first light has a peak wavelength within a predetermined wavelength range including a wavelength achieving a largest value of a hemoglobin absorption coefficient,
a second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and
a third light has a peak wavelength between the peak wavelength of the first light and the peak wavelength of the second light, and involves a larger scattering coefficient in biological tissue than a scattering coefficient of the second light,
the operating method comprising:
generating illumination light including the first light, second light, and third light;
capturing an image based on return light from the biological tissue irradiated with the illumination light; and
performing image processing based on a captured first image, second image, and third image respectively corresponding to the first light, second light, and third light.

According to another aspect of the disclosure, there is provided a non-transitory information storage medium, wherein
a first light has a peak wavelength within a predetermined wavelength range including a wavelength achieving a largest value of a hemoglobin absorption coefficient,
a second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and
a third light has a peak wavelength between the peak wavelength of the first light and the peak wavelength of the second light, and involves a larger scattering coefficient in biological tissue than a scattering coefficient of the second light,
the non-transitory information storage medium storing a program that causes a computer to execute:
generating illumination light including the first light, second light, and third light;
capturing an image based on return light from the biological tissue irradiated with the illumination light; and
performing image processing based on a captured first image, second image, and third image respectively corresponding to the first light, second light, and third light.

DESCRIPTION OF EXEMPLARY EMBODIMENTS

Figure 1:
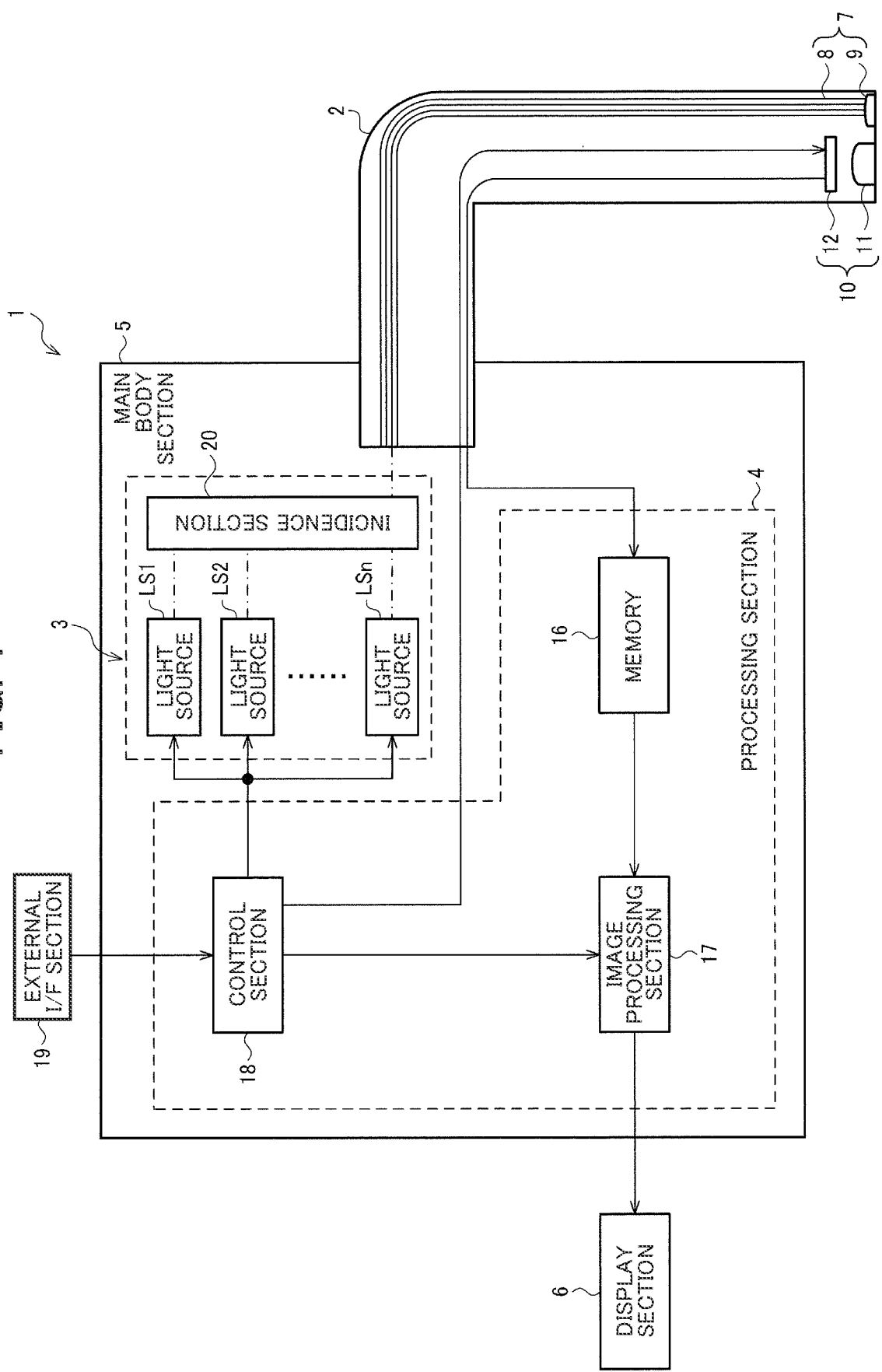
FIG. 1 is a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 is a configuration example of an endoscope apparatus 1. The endoscope apparatus 1 includes a main body section 5, an insertion section 2 detachable to the main body section via a connector, a display section 6 configured to display an image output by the main body section 5, and an external I/F section 19. The main body section 5 is also referred to as a controller, a control device, or a processing device. The insertion section 2 is also referred to as a scope. The display section 6 is also referred to as a display device or a display.

The insertion section 2 is inserted into a living body to illuminate and image tissue. In the present embodiment, the tissue is assumed to be an upper digestive tract such as the gullet or stomach, however, an object to be observed with the endoscope apparatus 1 is not limited to the upper digestive tract. The insertion section 2 includes an illumination optical system 7 configured to emit illumination light to an object and an imaging section 10 configured to capture an image of reflected light from the object. The imaging section 10 is also referred to as an imaging optical system or an imaging device.

The illumination optical system 7 includes a light guide cable 8 configured to guide the illumination light and an illumination lens 9 configured to diffuse the illumination light guided by the light guide cable 8 toward the object. The imaging section 10 includes an objective lens 11 configured to form an image of the object and an image sensor 12 configured to capture the image formed by the objective lens 11. The image sensor 12 is a monochrome image sensor or a color image sensor such as a complementary metal-oxide semiconductor (CMOS) image sensor or a charge-coupled device (CCD) image sensor.

The main body section 5 controls the endoscope apparatus 1 and performs image processing. The main body section 5 includes an illumination section 3 configured to generate illumination light and a processing section 4. The illumination section 3 is also referred to as an illumination device. The processing section 4 is also referred to as a processing circuit or a processing device.

The illumination section 3 includes light sources LS1 to LSn and an incidence section 20. "n" is an integer of 3 or larger. Each of the light sources LS1 to LSn emits a light of a predetermined spectrum. Each of the light sources LS1 to LSn is a light emitting diode (LED) or a laser, for example. The incidence section 20 makes the lights emitted from the light sources LS1 to LSn enter the light guide cable 8. The incidence section 20 includes a mirror and a dichroic mirror, for example.

The processing section 4 includes a memory 16 configured to store images captured by the image sensor 12, an image processing section 17 configured to process the images input from the memory 16, and a control section 18 configured to control the endoscope apparatus 1. The image processing section 17 is also referred to as an image processing circuit or an image processing device. The control section 18 is also referred to as a control circuit or a control device.

The control section 18 controls timing of image capturing by the image sensor 12, operation of the image processing section 17, and timing of light emission by the light sources LS1 to LSn. The control section 18 also controls the endoscope apparatus 1 based on operation information input from the external I/F section 19. The external I/F section 19 is an operation device used by a user to operate the endoscope apparatus 1, and includes a button, a dial, or a touch panel, for example. The external I/F section 19 may be disposed to at least one of the insertion section 2, the main body section 5 and the display section 6.

In the present embodiment, image capturing is performed by a frame sequential method, for example. In the frame sequential method, a plurality of lights are sequentially emitted to the object, and an object image is captured when each of the plurality of lights is emitted. Specifically, the control section 18 causes the light sources LS1 to LSn to sequentially emit a light one by one, and the image sensor 12 performs image capturing at each timing of light emission. The number of light sources caused to emit light at one emitting timing is not limited to one, but two or more light sources may be caused to simultaneously emit lights at one emitting timing.

The memory 16 stores the images captured at respective emitting timings. For example, when the light sources LS1 to LSn are caused to sequentially emit lights one by one, the memory 16 stores n number of captured images. The n number of captured images are images captured when the light sources LS1 to LSn emit the lights. Memory content of the memory 16 is updated every time when the images are sequentially captured by the frame sequential method. The number of frames stored in the memory 16 is not limited to n. The memory 16 may be configured to store any number of frames necessary for the image processing.

The image processing section 17 generates a display image from the captured images stored in the memory 16. As will be described later, the display image is basically a white light image. The white light image is an image acquired when white light is emitted to the object, or an image regarded as equivalent to such an image. One frame of the white light image is generated every time when the images are captured by the frame sequential method, whereby a video is generated, for example. The image processing section 17 also performs a highlighting process to the display image based on the captured images stored in the memory 16. The image processing section 17 outputs the display image applied with the highlighting process to the display section 6. The display section 6 is a liquid crystal display, for example. Details of the image processing section 17 will be described later.

Although the frame sequential method is described above as an example, the light sources LS1 to LSn may be caused to simultaneously emit the lights. In such a case, an image sensor having a color filter for each pixel is used as the image sensor 12. The image processing section 17 extracts images in respective color channels from a captured image and performs image processing based on the images in respective color channels. For example, when a color filter lets the light from the light source LS1 pass through, an image of a color channel corresponding to this color filter can be regarded as a captured image when the light from the light source LS1 is emitted on the object.

2. Illumination Section

Figure 2:
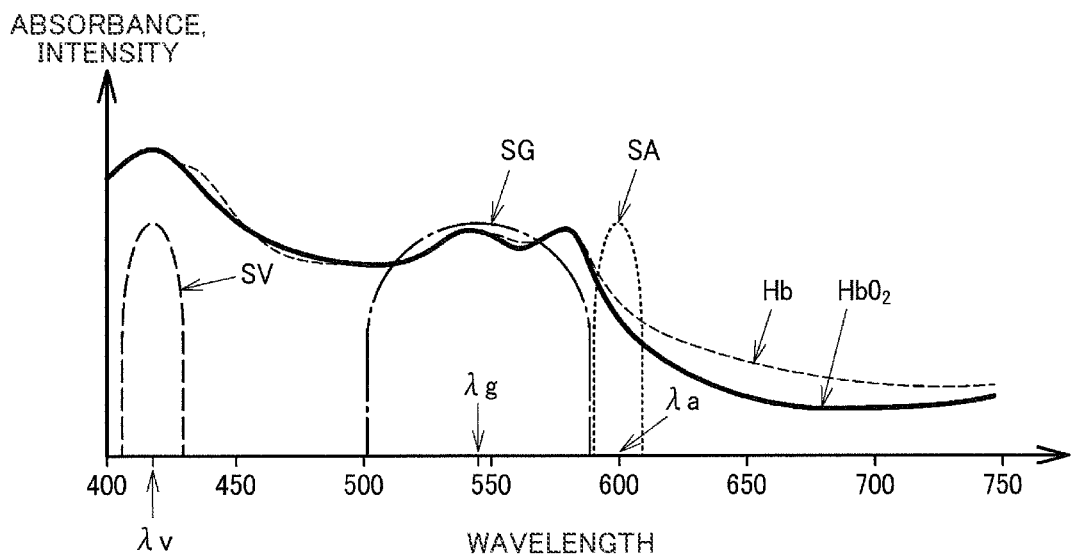
FIG. 2 is a first characteristics example of illumination light generated by an illumination section.

FIG. 2 is a first characteristics example of the illumination light generated by the illumination section 3. In FIG. 2, $HbO_2$ represents an absorbance spectrum of oxidized hemoglobin and Hb represents an absorbance spectrum of hemoglobin. SV represents an intensity spectrum of the light emitted from the light source LS1, SG represents an intensity spectrum of the light emitted from the light source LS2, and SA represents an intensity spectrum of the light emitted from the light source LS3. In this example, n is three (n=3). Description is given hereinafter with an example of the absorbance spectrum of the oxidized hemoglobin, and the oxidized hemoglobin is simply referred to as hemoglobin.

The spectrum SV has a violet wavelength band. Specifically, the spectrum SV has a peak at a peak wavelength $\lambda v$ of 415 nm ($\lambda v$=415 nm). The peak wavelength is a wavelength having highest light intensity. The wavelength of 415 nm is a wavelength having highest hemoglobin absorbance. The spectrum SV has a narrowband. For example, a half-value width is in a range from a few nm to some tens nm. The peak wavelength $\lambda v$ is not limited to 415 nm. For example, the peak wavelength $\lambda v$ is within a range of 415±20 nm, preferably within a range of 415±10 nm. In addition, the spectrum SV is not limited to the narrowband, but may be any spectrum as long as it has a peak at the wavelength $\lambda v$.

The spectrum SG has a green wavelength band. Specifically, the spectrum SG has a wavelength band from 500 to 580 nm, and a peak wavelength $\lambda g$ is around 540 nm. The spectrum SG only needs to have a wavelength band regarded as green, and is not limited to have the above-mentioned wavelength band or the peak wavelength. Specifically, the spectrum SG only needs to have the peak wavelength $\lambda g$ between the peak wavelength $\lambda v$ of the spectrum SV and a peak wavelength $\lambda a$ of the spectrum SA.

The spectrum SA has an amber or brown wavelength band. Specifically, the spectrum SA has a peak at a peak wavelength $\lambda a$ of 600 nm ($\lambda a$=600 nm). The spectrum SA has a narrowband. For example, a half-value width is in a range from a few nm to some tens nm. The spectrum of the hemoglobin achieves a maximum value at around 580 nm and a smallest value at around 670 nm. The absorbance monotonously decreases between the maximum value and a minimum value. The peak wavelength $\lambda a$ of 600 nm ($\lambda a$=600 nm) is between 580 nm where the spectrum of the hemoglobin achieves the maximum value and 670 nm where the spectrum of the hemoglobin achieves the minimum value. The peak wavelength $\lambda a$ is not limited to 600 nm. Specifically, it is preferable that the peak wavelength $\lambda a$ separate from the spectrum SG to a long wavelength side and the hemoglobin absorbance be as high as possible at the peak wavelength $\lambda a$. For example, the peak wavelength $\lambda a$ may be a wavelength within a range of 580 to 630 nm.

When the frame sequential method is used, the light sources LS1, LS2, and LS3 sequentially emit lights to sequentially apply the light of the spectrum SV, the light of the spectrum SG, and the light of the spectrum SA to the object. An order to apply the light of the spectrum SV, the light of the spectrum SG, and the light of the spectrum SA is not limited to this, but may be any order. In addition, an illumination method is not limited to the frame sequential method as mentioned above.

Figure 3:
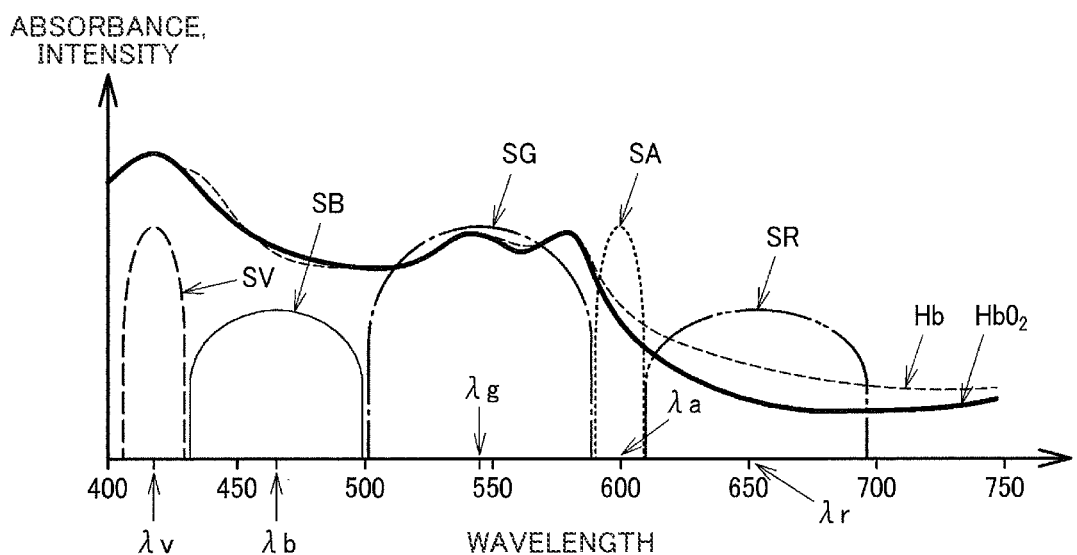
FIG. 3 is a second characteristics example of the illumination light generated by the illumination section.

FIG. 3 is a second characteristics example of the illumination light generated by the illumination section 3. The spectra described referring to FIG. 2 are denoted with the same reference signs, and the description thereof is omitted. In FIG. 3, SB represents an intensity spectrum of light emitted from a light source LS4, and SR represents an intensity spectrum of light emitted from a light source LS5. In this example, n is five (n=5).

The spectrum SB has a blue wavelength band. Specifically, the spectrum SB has a wavelength band from 430 to 500 nm, and a peak wavelength $\lambda b$ is around 465 nm. The spectrum SB only needs to have a wavelength band regarded as blue, and is not limited to have the above-mentioned wavelength band or the peak wavelength. Specifically, the spectrum SB only needs to have the peak wavelength $\lambda b$ between the peak wavelength $\lambda g$ of the spectrum SG and the peak wavelength $\lambda v$ of the spectrum SV.

The spectrum SR has a red wavelength band. Specifically, the spectrum SR has a wavelength band from 610 to 700 nm, and a peak wavelength $\lambda r$ is around 655 nm. The spectrum SR only needs to have a wavelength band regarded as red, and is not limited to have the above-mentioned wavelength band or the peak wavelength. Specifically, the spectrum SR only needs to have the peak wavelength $\lambda r$ on a long wavelength side compared with the peak wavelength $\lambda a$ of the spectrum SA.

When the frame sequential method is used, the light sources LS1, LS2, LS3, LS4, and LS5 sequentially emit lights to sequentially apply lights of the spectrum SV, spectrum SG, spectrum SA, spectrum SB, and spectrum SR to the object. An order to apply the lights of the spectrum SV, spectrum SG, spectrum SA, spectrum SB, and spectrum SR is not limited to this, but may be any order. In addition, the illumination method is not limited to the frame sequential method as mentioned above.

3. Image Processing Method

The lights as described above are applied to the object and images of the object are captured to acquire the images in respective wavelength bands. A method of the image processing based on these images is described hereinafter. In the following description, the light of the spectrum SV is referred to as an SV light, for example. An image captured when the light of the spectrum SV is applied is referred to as an SV image, for example.

Figure 4:
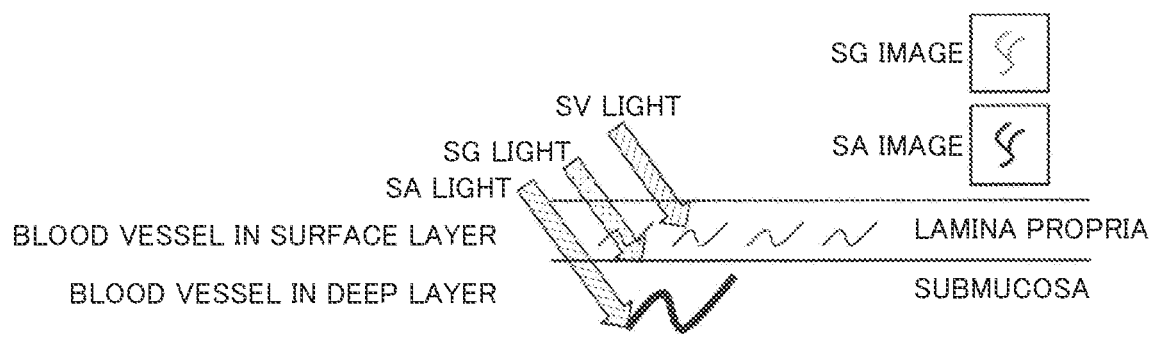
FIG. 4 is a diagram illustrating an image acquired when the illumination light is emitted on normal gastric mucosa.

Referring to FIG. 4, images acquired when the SV light, SG light, and SA light are applied to normal gastric mucosa are described.

Scattering of visible light in a living body becomes stronger as a wavelength is shorter. When light enters the living body, intensity of the light is attenuated by scattering. Thus, a depth that the light can reach becomes shallower as scattering is stronger. That is, the depth that the light can reach in the living body becomes shallower as the wavelength is shorter.

As illustrated in FIG. 4, since the SV light has the wavelength shorter than the wavelengths of the SG light and the SA light, the SV light only reaches a shallower mucosal layer compared with the depth reached by the SG light and the SA light. Specifically, a stomach wall includes lamina propria as a surface layer and submucosa as a layer deeper than the lamina propria. The SV light is scattered by the lamina propria and is also absorbed by hemoglobin present in the lamina propria. Since the lamina propria includes a capillary, the SV image reflects a degree of hyperemia of the lamina propria. That is, since absorption of the SV light increases as the lamina propria is more congested, the SV image becomes darker.

The SA light has the wavelength longer than the wavelengths of the SV light and the SG light, and thus the SA light reaches a deeper mucosal layer compared with the depth reached by the SV light and the SG light. Specifically, the SA light reaches the submucosa. Accordingly, the SA light is scattered by the lamina propria and the submucosa, and is also absorbed by hemoglobin present in the lamina propria and the submucosa. Since the submucosa includes a thicker blood vessel compared with the capillary in the lamina propria, the SA image includes the blood vessel in the submucosa. The SA light is influenced by scattering and absorption in the lamina propria. However, since the SA light has the long wavelength, a degree of scattering is small, and thus the SA image can include a blood vessel image in the submucosa.

The SG light has the wavelength longer than the wavelength of the SV light and shorter than the wavelength of the SA light, and thus the SG light reaches a part deeper than a part reached by the SV light and shallower than a part reached by the SA light. Specifically, the SG light reaches a depth in between the lamina propria and the submucosa, and thus the SG light partially reaches the submucosa. Accordingly, the SG image includes the blood vessel image in the submucosa, however, the blood vessel image in the SG image has contrast lower than contrast of the blood vessel image in the SA image. That is, although the SG image includes the blood vessel in the submucosa, the blood vessel image is fainter than the blood vessel image in the SA image.

Figure 5:
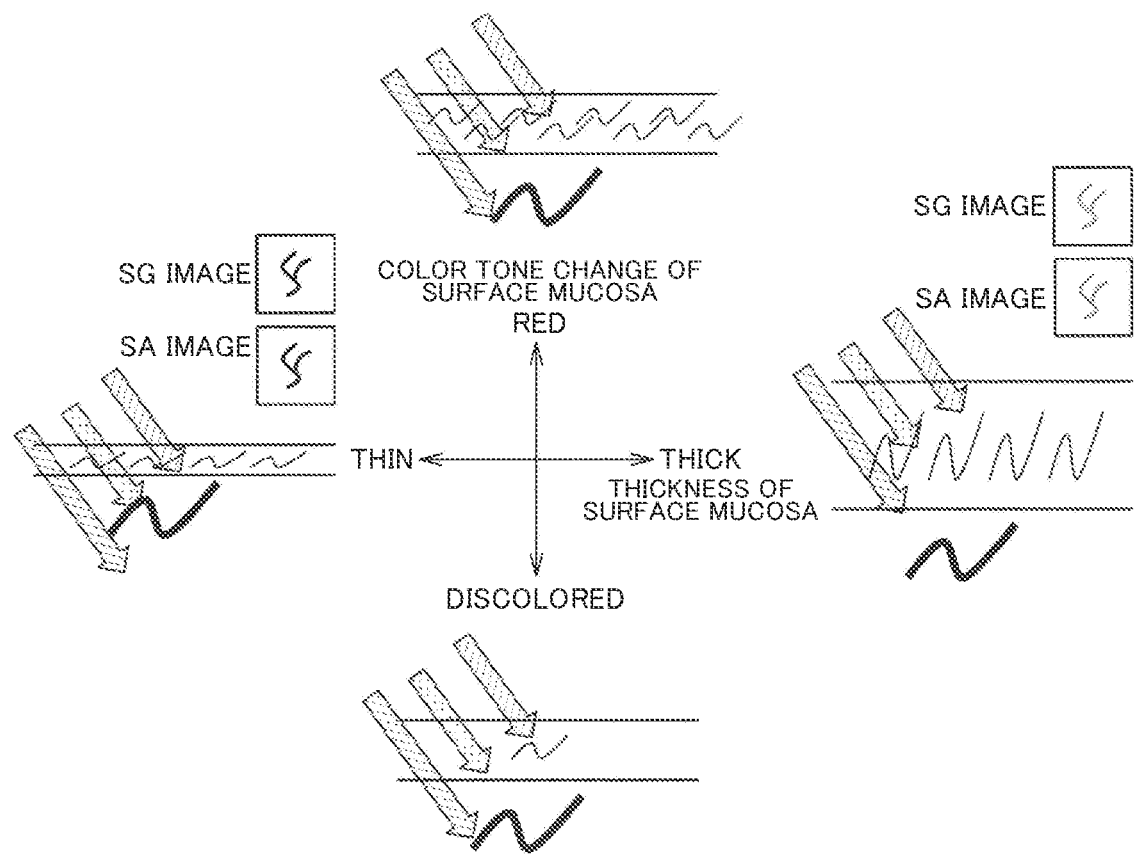
FIG. 5 is a diagram illustrating images acquired when the illumination light is emitted on abnormal gastric mucosa.

Referring to FIG. 5, images acquired when the SV light, SG light, and SA light are applied to abnormal gastric mucosa are described next.

As illustrated in an upper part and a lower part of FIG. 5, the SV light is absorbed by a capillary in the lamina propria. When the gastric mucosa is seen in a white light image, redness of the mucosa changes in accordance with density of the capillaries in the lamina propria and the degree of hyperemia of the capillary. That is, the SV image provides information on a color tone of surface mucosa. Specifically, as illustrated in the upper part of FIG. 5, when the lamina propria is congested due to inflammation or the like, the gastric mucosa appears to have redness in the white light image. At this time, absorption of the SV light in the lamina propria is high, and thus the SV image becomes darker. On the contrary, as illustrated in the lower part of FIG. 5, when the number of capillaries in the lamina propria declines, the gastric mucosa appears to be discolored in the white light image. At this time, absorption of the SV light in the lamina propria is low, and thus the SV image becomes brighter. Thus, brightness of the SV image shows a change in color tone of the surface mucosa.

As illustrated in a right part and a left part of FIG. 5, the SG light and the SA light reach the deeper parts compared with the part reached by the SV light. At this time, thickness of the lamina propria influences whether the SG light and the SA light reach the submucosa. That is, the SG image and the SA image provide information on thickness of the surface mucosa. Specifically, as illustrated in the left part of FIG. 5, when the lamina propria becomes thin due to atrophy or the like, the SG light and the SA light reach the submucosa. Accordingly, the blood vessel image in the submucosa has high contrast in both the SG image and the SA image. On the contrary, as illustrated in the right part of FIG. 5, when the lamina propria becomes thick, the SG light and the SA light are scattered by the thick lamina propria, and quantity of lights that reach the submucosa becomes small. Accordingly, the blood vessel image in the submucosa has low contrast in both the SG image and the SA image.

As a result, in the present embodiment, the SV image can provide the information on the change in color tone of the surface mucosa. The SG image and the SA image can provide the information on the thickness of the surface mucosa. In accordance with the present embodiment, such information is used to perform a highlighting process to the white light image, which enables diagnostic support by imaging when physicians diagnose inflammatory diseases of the stomach.

There are conventional methods for diagnosing gastric diseases with an endoscope apparatus, as described below.

For example, atrophic gastritis has characteristics that the surface mucosa becomes thin. In order to diagnose this gastritis, a physician checks a visible vascular pattern in the white light image. The visible vascular pattern is a blood vessel image seen through the mucosa. That is, since the surface mucosa is thin in the atrophic gastritis, the physician confirms by image observation that the blood vessel in the submucosa can be seen through the surface mucosa. Furthermore, enlarged-fold gastritis has characteristics that folds of the mucosa become thick. The folds mean wrinkles or creases. In order to diagnose this gastritis, the physician confirms that the folds of the stomach wall do not disappear when the stomach is expanded by supplied air. Furthermore, scirrhous stomach cancer has characteristics that cancer cells spread beneath the mucosa and a lot of fibrous tissue is generated. In order to diagnose this stomach cancer, the physician confirms that tortuous folds are running in high density, and a space between the folds is not widened when the stomach is expanded by supplied air.

Although the conventional methods described above can be used to diagnose the inflammatory diseases of the stomach, there is no conventional method for appropriately supporting diagnosis of the various inflammatory diseases of the stomach by an imaging method such as image highlighting. In addition, there is no conventional method for supporting diagnosis of the various inflammatory diseases of the stomach by imaging before the diseases progress to a state that can be diagnosed by the conventional diagnosing methods.

Now, in accordance with the present embodiment, the endoscope apparatus 1 includes the illumination section 3 configured to generate illumination light including a first light, second light, and third light, the imaging section 10 configured to capture an image based on return light from biological tissue irradiated with the illumination light, and the image processing section 17 configured to perform the image processing based on a first image, second image, and third image that are captured by the imaging section 10 and respectively correspond to the first light, second light, and third light. The first light has a peak wavelength within a predetermined wavelength range including a wavelength achieving a largest value of a hemoglobin absorption coefficient. In FIGS. 2 and 3, the first light corresponds to the SV light, and the peak wavelength $\lambda v$ of the SV light is 415 nm ($\lambda v$=415 nm). The second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value. In FIGS. 2 and 3, the second light corresponds to the SA light, and the peak wavelength λa of the SA light is 600 nm. The wavelength achieving the smallest value of the hemoglobin absorption coefficient is around 670 nm. The wavelength achieving the first maximum value of the hemoglobin absorption coefficient on the shorter wavelength side of the wavelength achieving the smallest value is around 580 nm. The third light has a peak wavelength between the peak wavelength of the first light and the peak wavelength of the second light, and involves a larger scattering coefficient in the biological tissue compared with a scattering coefficient of the second light. In FIGS. 2 and 3, the third light corresponds to the SG light, and the peak wavelength λg of the SG light is around 540 nm.

In accordance with the present embodiment, the SV image can be acquired as the first image corresponding to the first light, the SA image can be acquired as the second image corresponding to the second light, and the SG image can be acquired as the third image corresponding to the third light. In addition, the information on the change in color tone of the surface mucosa can be acquired from the SV image, and the information on the thickness of the surface mucosa can be acquired from the SG image and the SA image. As a result, it is possible to support diagnosing various inflammatory diseases of the stomach by imaging. This is described hereinafter referring to FIG. 6.

Figure 6:
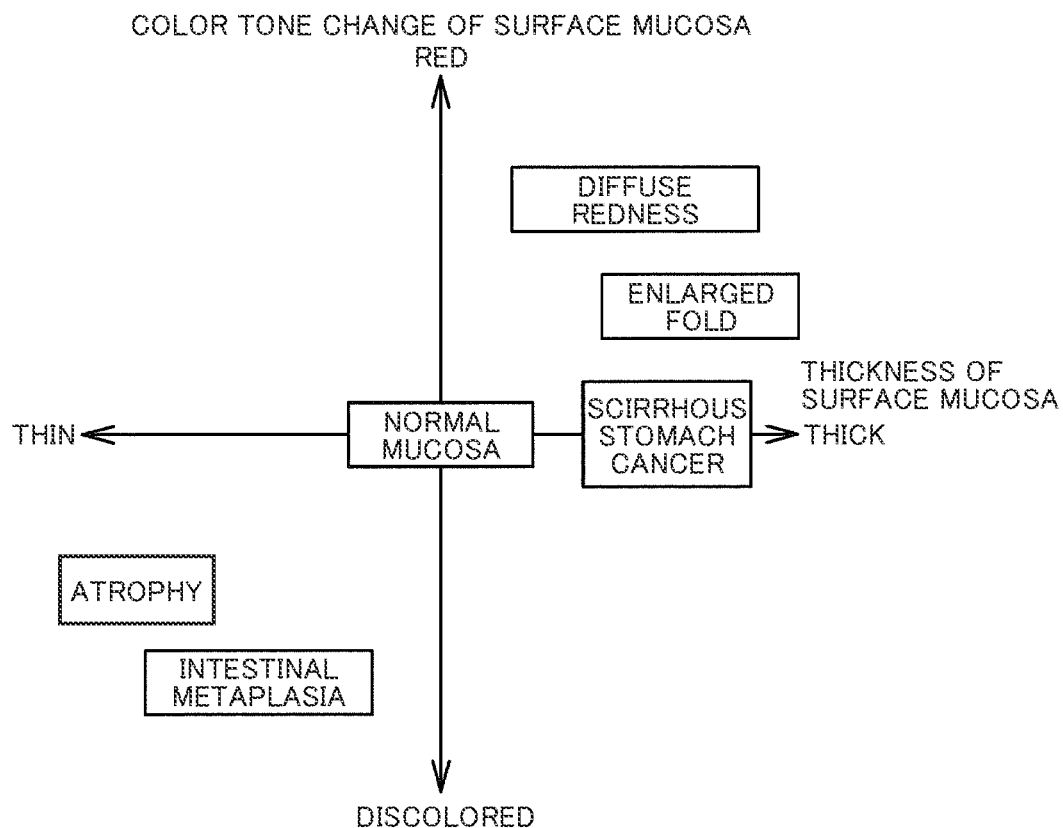
FIG. 6 is a diagram illustrating a relationship of thickness of surface mucosa and a change in color tone of the surface mucosa with various inflammatory diseases of a stomach.

FIG. 6 is a diagram illustrating a relationship of the thickness of the surface mucosa and the change in color tone of the surface mucosa with various inflammatory diseases of the stomach. In FIG. 6, a horizontal axis represents the thickness of the surface mucosa, and a vertical axis represents the change in color tone of the surface mucosa. For example, when findings from image observation indicate that the surface mucosa is thick and the color tone of the surface mucosa is close to the color tone of the normal mucosa, a possibility of scirrhous stomach cancer is suggested.

In accordance with the present embodiment, the change in color tone of the surface mucosa can be highlighted based on the SV image. In addition, the thickness of the surface mucosa can be highlighted based on the SG image and the SA image. As a result, it is possible to display and highlight characteristics of the change in color tone of the surface mucosa and the thickness of the surface mucosa, and to provide diagnostic support for diagnosing inflammatory diseases of the stomach by the image.

Furthermore, in accordance with the present embodiment, the diagnostic support uses the method by imaging such as image highlighting, instead of the method of observing expansion of the folds by supplied air, or the like. Accordingly, the diagnostic support can be performed at a stage where the thickness of the surface mucosa is gradually increasing, for example, before the disease can be diagnosed by the method of observing expansion of the folds by supplied air or the like. That is, with the method in accordance with the present embodiment, it is possible to provide supporting information for diagnosing the state of the disease before or during the progress of the disease.

Furthermore, in accordance with the present embodiment, the SV light (the first light) has the peak wavelength within the predetermined wavelength range of 415±20 nm. The SA light (the second light) has the peak wavelength within the range of 600±20 nm.

As described referring to FIGS. 2 and 3, the wavelength of 415 nm achieves the largest value of the hemoglobin absorption coefficient. Setting the peak wavelength of the SV light within the range of 415±20 nm allows the SV light to be absorbed by the hemoglobin with a large light absorption coefficient. As a result, the brightness of the SV image highly sensitively changes in accordance with the change in color tone of the surface mucosa, and thus the change in color tone of the surface mucosa can be effectively highlighted based on the brightness of the SV image.

Furthermore, as described referring to FIGS. 2 and 3, the wavelength of 600 nm is between the maximum value around 580 nm and the smallest value around 680 nm in the absorbance spectrum of hemoglobin. That is, the light having the wavelength of 600 nm is on the long wavelength side having a larger scattering coefficient compared with a scattering coefficient of the SG light, and has a light absorption coefficient of hemoglobin larger than the smallest value. As a result, setting the peak wavelength of the SA light within the range of 600±20 nm allows the SA light to reach the part of the mucosa deeper than the part reached by the SG light, and also allows the SA light to be used for image capturing of the blood vessel in the submucosa. As described referring to FIG. 5, since the SG light and the SA light reach different depths, and enable image capturing of the blood vessel, the SG image and the SA image can provide the information on the thickness of the surface mucosa.

Furthermore, in accordance with the present embodiment, the SV light and the SA light are narrowband lights each having a wavelength band narrower than a wavelength band of the SG light (the third light). For example, the wavelength bands of the narrowband lights are in a range from a few nm to some tens nm.

The scattering coefficient in the living body is determined in accordance with the wavelength. The depth reached by a light in the living body can be controlled more easily in a case of a narrowband light compared with a case of a broadband light. As a result, using the narrowband light as the SV light and the SA light can highlight the change in color tone of the surface mucosa and the thickness of the surface mucosa more accurately.

Furthermore, in accordance with the present embodiment, the image processing section 17 performs a process of highlighting the color tone of the mucosa in the biological tissue, and a process of highlighting the blood vessel in the submucosa in the biological tissue, based on the SV image (the first image), the SA image (the second image), and the SG image (the third image). Specifically, the image processing section 17 performs the process of highlighting the color tone of the mucosa in the biological tissue based on the SV image with respect to the white light image. The image processing section 17 also performs the process of highlighting the blood vessel in the submucosa in the biological tissue based on the SA image and the SG image with respect to the white light image.

In accordance with the present embodiment, the color tone of the mucosa in the biological tissue can be highlighted based on the SV image whose brightness changes in accordance with the color tone of the surface mucosa. The blood vessel in the submucosa in the biological tissue can be highlighted based on the SG image and the SA image whose contrast of the blood vessel image changes in accordance with the thickness of the surface mucosa. As a result, as described referring to FIG. 6, it is possible to support diagnosing various inflammatory diseases of the stomach by imaging using the change in color tone of the surface mucosa and the thickness of the surface mucosa as indexes.

Furthermore, in accordance with the present embodiment, the image processing section 17 highlights structural information in a display image based on the SA image and the SG image. The display image is a white light image generated from the captured images. In the example in FIG. 2, a white light image is generated from the SV image, SG image, and SA image. In the example in FIG. 3, a white light image is generated from the SB image, SG image, and SR image. Alternatively, a white light image may be generated from the SV image, SB image, SG image, SA image, and SR image.

Highlighting the structural information in the display image based on the SA image and the SG image can highlight the blood vessel in the submucosa in the biological tissue. The blood vessel in the submucosa looks different in accordance with the thickness of the surface mucosa, and thus highlighting the blood vessel in the submucosa can present the thickness of the surface mucosa as supporting information.

Furthermore, in accordance with the present embodiment, the image processing section 17 extracts a frequency component in a predetermined frequency band from the SA image as a first frequency component, and a frequency component in a predetermined frequency band from the SG image as a second frequency component. The predetermined frequency band applied to the SA image and the predetermined frequency band applied to the SG image are the same, for example, but may be different. The image processing section 17 sets a highlighting coefficient based on a correlation between the first frequency component and the second frequency component, and highlights the structural information in the display image by using the highlighting coefficient.

The predetermined frequency band is set to a frequency band that enables extraction of the blood vessel in the submucosa from the SA image and the SG image. The SA image and the SG image include the same blood vessel image, however, the contrast varies in accordance with the thickness of the surface mucosa. That is, when the surface mucosa is thin, the contrast of the blood vessel image is high in both the images. When the surface mucosa is thick, the contrast is low in both the images. When the surface mucosa has normal thickness, the contrast of the blood vessel image is low in the SG image and high in the SA image. The image processing section 17 sets the highlighting coefficient for structural highlighting based on this correlation between the blood vessel images in the SA image and the SG image. Specifically, the image processing section 17 sets a highlighting coefficient such that the blood vessel in the submucosa is highlighted more as the surface mucosa is thinner. As a result, since the blood vessel in the submucosa can be highlighted more as the surface mucosa is thinner, the thickness of the surface mucosa can be easily read from the display image.

Furthermore, in accordance with the present embodiment, the image processing section 17 makes the highlighting coefficient larger as the first frequency component is larger, and also makes the highlighting coefficient larger as the second frequency component is larger. That is, when both the first frequency component and the second frequency component are large, the highlighting coefficient becomes large, and when both the first frequency component and the second frequency component are small, the highlighting coefficient becomes small.

Accordingly, the highlighting coefficient becomes larger as the contrast of the blood vessel image in the SA image is higher, and the highlighting coefficient also becomes larger as the contrast of the blood vessel image in the SG image is higher. As a result, the blood vessel in the submucosa can be highlighted more as the surface mucosa is thinner.

Furthermore, in accordance with the present embodiment, the image processing section 17 highlights color information in the display image based on the SV image. Specifically, the image processing section 17 highlights the redness of the mucosa so as to make it look more brightly red. The image processing section 17 also highlights the discoloring of the mucosa so as to make it look more discolored.

Highlighting the color information in the display image based on the SV image can highlight the color tone of the surface mucosa in the biological tissue. Highlighting the color tone of the surface mucosa can present the density of the capillaries in the surface mucosa and the degree of hyperemia of the capillary as the supporting information. This information indicates inflammation of the surface mucosa, a state of the capillary in the surface mucosa, or the like. Presenting the supporting information related to this information can support diagnosing the inflammatory diseases of the stomach.

Furthermore, in accordance with the present embodiment, the image processing section 17 sets a highlighting coefficient based on a signal value of the SV image and highlights the color information by using the highlighting coefficient. The signal value is also referred to as a pixel value. Alternatively, the signal value may be an average pixel value in a local region of the SV image. Alternatively, a smoothing process may be performed to the SV image and a pixel value in a resultant image may be used as the signal value.

As described above, the signal value of the SV image varies in accordance with the color tone of the surface mucosa. Thus, setting the highlighting coefficient based on the signal value of the SV image can highlight the color tone of the surface mucosa.

Furthermore, in accordance with the present embodiment, the image processing section 17 makes the highlighting coefficient larger as the signal value of the SV image is lower.

As described above, when the surface mucosa has redness, an absorption quantity of the SV light increases, and thus the signal value of the SV image becomes lower. When the surface mucosa discolors, the absorption quantity of the SV light decreases, and thus the signal value of the SV image becomes higher. Making the highlighting coefficient larger as the signal value of the SV image is lower can highlight the redness of the mucosa to look more brightly red. This can also highlight the discoloring of the mucosa to look more discolored.

The endoscope apparatus in accordance with the present embodiment may have a configuration described below. That is, the endoscope apparatus in accordance with the present embodiment includes a memory configured to store information and a processor configured to operate based on the information stored in the memory. The information includes, for example, a program and various data. The processor includes hardware. The processor performs the image processing based on the first image, second image, and third image that are captured by the imaging section 10 and respectively correspond to the first light, second light, and third light.

The processor may have functions of sections each implemented by individual hardware, or the functions of sections each implemented by integrated hardware, for example. The processor may include hardware, and the hardware may include at least one of a circuit that processes a digital signal and a circuit that processes an analog signal. For example, the processor may include one or more circuit devices mounted on a circuit board, or one or more circuit elements. The one or more circuit devices are an integrated circuit (IC), for example. The one or more circuit elements are a resistor or a capacitor, for example. The processor may be a central processing unit (CPU), for example. However, the processor is not limited to the CPU, but may be any other processor of various types such as a graphics processing unit (GPU) or a digital signal processor (DSP). The processor may be a hardware circuit that includes an application-specific integrated circuit (ASIC). The processor may include an amplifier circuit, a filter circuit, or the like that processes an analog signal. The memory may be a semiconductor memory such as a static random-access memory (SRAM) or a dynamic random-access memory (DRAM), or may be a register. The memory may be a magnetic storage device such as a hard disk drive (HDD), or may be an optical storage device such as an optical disc device. For example, the memory may store a computer-readable instruction. A function of each of the sections of the endoscope apparatus is implemented as a process when the processor executes the instruction. The instruction may be an instruction set that is included in a program, or may be an instruction that instructs the hardware circuit included in the processor to operate. The sections of the endoscope apparatus correspond to the control section 18 and the image processing section 17 illustrated in FIG. 1, for example. The memory corresponds to the memory 16 illustrated in FIG. 1 or a memory not illustrated, for example.

Each of the sections of the endoscope apparatus in accordance with the present embodiment may be implemented as a module of a program that operates on the processor. For example, the image processing section 17 is implemented by an image processing module that performs the image processing based on the first image, second image, and third image that are captured by the imaging section 10 and respectively correspond to the first light, second light, and third light.

Furthermore, the program implementing the processes performed by the sections of the endoscope apparatus in accordance with the present embodiment can be stored, for example, in a computer-readable information storage medium. The information storage medium can be implemented by an optical disk, a memory card, a HDD, or a semiconductor memory (a read-only memory [ROM]), for example. The semiconductor memory is a ROM, for example. The image processing section 17 and the control section 18 of the endoscope apparatus perform various processes in accordance with the present embodiment based on the program and data stored in the information storage medium. That is, the information storage medium stores the program causing a computer to function as the sections of the endoscope apparatus in accordance with the present embodiment. The computer is a device including an input device, a processing section, a storage section, and an output section. The program causes the computer to execute the processes of the sections.

4. Details of Image Processing Section

Figure 7:
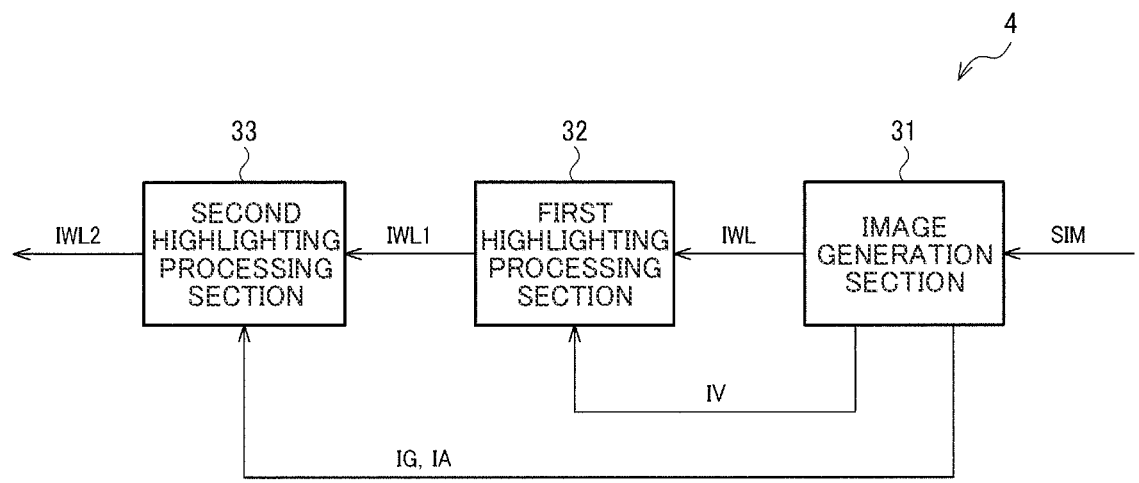
FIG. 7 is a detailed configuration example of an image processing section.

FIG. 7 is a detailed configuration example of the image processing section 17. The image processing section 17 includes an image generation section 31, a first highlighting processing section 32, and a second highlighting processing section 33. For example, when the image processing section 17 includes the DSP, the DSP performs the processes of the image generation section 31, the first highlighting processing section 32, and the second highlighting processing section 33 in a time-division manner. Alternatively, each of the image generation section 31, the first highlighting processing section 32, and the second highlighting processing section 33 may include an individual circuit.

The image generation section 31 receives input of captured images SIM from the memory 16 illustrated in FIG. 1. The image processing section 17 generates a white light image IWL from the captured images SIM. The image processing section 17 also outputs the SV image IV to the first highlighting processing section 32, and the SG image IG and the SA image IA to the second highlighting processing section 33. In the example in FIG. 2, the image processing section 17 combines the SV image, SG image, and SA image to generate the white light image IWL. In the example in FIG. 3, the image processing section 17 combines the SB image, SG image, and SR image to generate the white light image IWL. Alternatively, the image processing section 17 may further use the SV image and the SA image. The image processing section 17 may perform various image processing such as gain processing to the images of respective wavelengths when generating the white light image IWL.

The first highlighting processing section 32 highlights the color information of the white light image IWL by calculation using the SV image IV. That is, the first highlighting processing section 32 highlights the redness in the white light image IWL in accordance with the signal value of the SV image IV. The first highlighting processing section 32 performs this highlighting process for each pixel or local region. That is, the first highlighting processing section 32 performs calculation for highlighting the redness in the white light image IWL with respect to a region having a high signal value in the SV image IV. The first highlighting processing section 32 outputs a resultant white light image IWL1 applied with the processing.

Specifically, the first highlighting processing section 32 sets a highlighting coefficient to increase chroma of the white light image BAIL when the signal value of the SV image IV is low. That is, when the signal value of the SV image IV is low, the density of the capillaries in the surface mucosa is high and the surface mucosa in the white light image IWL is reddish. Accordingly, when the signal value of the SV image IV is low, the first highlighting processing section 32 highlights the redness. For example, the first highlighting processing section 32 converts the white light image IWL into a YCrCb signal and multiplies a Cr signal of the YCrCb signal by a gain. The gain is inversely proportional to the signal value of the SV image. The gain also corresponds to the highlighting coefficient.

Furthermore, the first highlighting processing section 32 sets a highlighting coefficient to reduce the chroma of the white light image IWL, when the signal value of the SV image IV is high. That is, when the signal value of the SV image IV is high, the density of the capillaries in the surface mucosa is low and the surface mucosa in the white light image IWL is discolored. Accordingly, when the signal value of the SV image IV is high, the first highlighting processing section 32 suppresses the redness of the surface mucosa and makes the surface mucosa whiter. For example, the first highlighting processing section 32 converts the white light image IWL into the YCrCb signal and multiplies the Cr signal of the YCrCb signal by a gain. The gain is inversely proportional to the signal value of the SV image and is one or smaller.

The second highlighting processing section 33 highlights the structural information in the white light image IWL1 by calculation using the SG image IG and the SA image IA. For example, the second highlighting processing section 33 extracts an edge of the blood vessel from the SA image IA by a bandpass filter as the first frequency component. The second highlighting processing section 33 also extracts an edge of the blood vessel from the SG image IG by the bandpass filter as the second frequency component. The second highlighting processing section 33 performs the structural highlighting of the blood vessel in the white light image IWL1 based on the first frequency component and the second frequency component.

Specifically, the second highlighting processing section 33 multiplies the first frequency component and the second frequency component, and uses a product of this multiplication as a highlighting coefficient. The second highlighting processing section 32 performs the multiplication for each pixel or local region. The second highlighting processing section 33 adds the highlighting coefficient to the white light image IWL1. For example, the second highlighting processing section 33 adds the highlighting coefficient to a G pixel value in the white light image IWL1.

When both the first frequency component and the second frequency component are large, the highlighting coefficient becomes large. That is, the blood vessel looks more highlighted in the white light image. On the contrary, when both the first frequency component and the second frequency component are small, the highlighting coefficient becomes small. That is, the blood vessel becomes more inconspicuous in the white light image. For example, the second highlighting processing section 33 may set a highlighting coefficient that varies in a nonlinear manner with respect to the product of the multiplication of the first frequency component and the second frequency component. Alternatively, the second highlighting processing section 33 may set a highlighting coefficient that varies in a quadratic function manner with respect to the product of the multiplication of the first frequency component and the second frequency component.

In FIG. 7, the structural highlighting is performed after the color highlighting, however, an order is not limited to this. That is, the color highlighting may be performed after the structural highlighting, or the color highlighting and the structural highlighting may be performed in parallel.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
   an illumination device configured to generate illumination light including a first light, a second light, and a third light;
   an imaging device configured to capture an image based on return light from biological tissue irradiated with the illumination light; and
   a processor configured to perform image processing based on a first image, second image, and third image, respectively corresponding to the first light, second light, and third light, captured by the imaging device;
   wherein the illumination device generates
   the first light having a peak wavelength within a predetermined wavelength range including a wavelength achieving a largest value of a hemoglobin absorption coefficient,
   the second light having a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and
   the third light having a peak wavelength between the peak wavelength of the first light and the peak wavelength of the second light, and involving a larger scattering coefficient in the biological tissue than a scattering coefficient of the second light in the biological tissue.

2. The endoscope apparatus as defined in claim 1, wherein the first light has the peak wavelength within a predetermined wavelength range of 415±20 nm, and the second light has the peak wavelength within a range of 600±20 nm.

3. The endoscope apparatus as defined in claim 1, wherein each of the first light and the second light is narrowband light having a wavelength band narrower than a wavelength band of the third light beam.

4. The endoscope apparatus as defined in claim 1, wherein the processor performs a process of highlighting a color tone of mucosa in the biological tissue, and a process of highlighting a blood vessel in submucosa in the biological tissue, based on the first image, second image, and third image.

5. The endoscope apparatus as defined in claim 1, wherein the processor highlights structural information in a display image, based on the second image and the third image.

6. The endoscope apparatus as defined in claim 5, wherein the processor extracts a frequency component in a predetermined frequency band from the second image as a first frequency component and a frequency component in a predetermined frequency band from the third image as a second frequency component, sets a highlighting coefficient based on a correlation between the first frequency component and the second frequency component, and highlights the structural information by using the highlighting coefficient.

7. The endoscope apparatus as defined in claim 6, wherein the processor makes the highlighting coefficient larger as the first frequency component is larger, and also makes the highlighting coefficient larger as the second frequency component is larger.

8. The endoscope apparatus as defined in claim 1, wherein the processor highlights color information in a display image based on the first image.

9. The endoscope apparatus as defined in claim 8, wherein the processor sets a highlighting coefficient based on a signal value of the first image, and highlights the color information by using the highlighting coefficient.

10. The endoscope apparatus as defined in claim 9, wherein the processor makes the highlighting coefficient larger as the signal value is lower.

11. An operating method of an endoscope apparatus, wherein a first light has a peak wavelength within a predetermined wavelength range including a wavelength achieving a largest value of a hemoglobin absorption coefficient, a second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and a third light has a peak wavelength between the peak wavelength of the first light and the peak wavelength of the second light, and involves a larger scattering coefficient in biological tissue than a scattering coefficient of the second light, the operating method comprising:

generating illumination light including the first light, second light, and third light;

capturing an image based on return light from the biological tissue irradiated with the illumination light; and performing image processing based on a captured first image, second image, and third image respectively corresponding to the first light, second light, and third light.

12. A non-transitory information storage medium, wherein a first light has a peak wavelength within a predetermined wavelength range including a wavelength achieving a largest value of a hemoglobin absorption coefficient, a second light has a peak wavelength between a wavelength achieving a smallest value of the hemoglobin absorption coefficient and a wavelength achieving a first maximum value of the hemoglobin absorption coefficient on a shorter wavelength side of the wavelength achieving the smallest value, and a third light has a peak wavelength between the peak wavelength of the first light and the peak wavelength of the second light, and involves a larger scattering coefficient in biological tissue than a scattering coefficient of the second light, the non-transitory information storage medium storing a program that causes a computer to execute:

generating illumination light including the first light, second light, and third light;

capturing an image based on return light from the biological tissue irradiated with the illumination light; and performing image processing based on a captured first image, second image, and third image respectively corresponding to the first light, second light, and third light.

* * * * *